US005393657A

United States Patent [19]
Letwin et al.

[11] Patent Number: 5,393,657
[45] Date of Patent: Feb. 28, 1995

[54] DETECTION OF RESIDUAL HOST CELL DNA BY PCR

[75] Inventors: Bruce W. Letwin, N. Andover; Melissa A. Jezuit, Winchester, both of Mass.

[73] Assignee: Genetics Institute, Inc., Cambridge, Mass.

[21] Appl. No.: 990,300

[22] Filed: Nov. 30, 1992

[51] Int. Cl.[6] .............................................. C12Q 1/68
[52] U.S. Cl. ...................................... 435/6; 435/91.2; 536/22.1; 536/23.1; 536/24.3; 536/24.31; 536/24.33; 935/77; 935/78; 935/88
[58] Field of Search ................... 435/6, 91, 91.1, 91.2; 436/501; 536/22.1, 23.1, 24.1, 24.2, 24.3, 24.33, 24.31, 24.32; 935/78, 88

[56] References Cited

FOREIGN PATENT DOCUMENTS

| | | |
|---|---|---|
| 0310251A2 | 4/1989 | European Pat. Off. |
| 0342717A2 | 11/1989 | European Pat. Off. |
| 0390518A2 | 10/1990 | European Pat. Off. |
| WO92/10566 | 6/1992 | WIPO |
| WO92/13101 | 8/1992 | WIPO |
| WO92/14844 | 11/1992 | WIPO |

OTHER PUBLICATIONS

Nelson et al. (1989) Proc. Natl Acad Sci (USA), vol. 86, pp. 6686–6690.

Anthony V. Cox et al., "Use of the polymerase chain reaction to detect spacer size heterogeneity in plant 5S-rRNA gene clustrs and to locate such clusters in wheat (*Triticum aestivum L.*)", *Theor. Appl. Genet* 83:684–690 (1992).

Kathleen D. Eisenach et al., "Polymerase Chain Reasction Amplification of a Repetitive DNA Sequence Specific for *Mycobacterium tuberculosis*" *J. of Infectious Diseases* 161: 977–981 (1990).

Mark Goldman et al., "Use of Polyerase Chain Reaction for Detecting DNA Contaminants in Pharmaceutical Recombinant Products" *Clinical Chemistry*, vol. 37, No. 9 pp. 1523–1525 (1991).

Susan R. Haynes et al., "The Chinese Hamster Alu—Equivalent Sequence: A Conserved, Highly Repetitious, Interspersed Deoxyribonucleic Acid Sequence in Mammals has a Structure Suggestive of a Transposable Element." *Molecular and Cellular Biology*, vol. 1, No. 7 pp. 573–583 (1981).

Walter E. Hill et al., "Polymerase Chain Reaction Identification of *Vibrio vulnificus* in Artificially Contaminated Oysters." *Applied and Environmental Microbiology* V. 57, No. 3, pp. 707–711 (1991).

Alec J. Jeffreys et al., "Hypervariable 'minisatellite' Regions in Human DNA" *Nature* vol. 314 pp. 67–72 (Mar. 1985).

Warren R. Jelinek et al., "Repetitive Sequences in Eukaryotic DNA and Their Expression" *Ann. Rev. Biochem.* 51: 813–44 (1982).

Offert Landt et al., "A General Method for Rapid Site-Directed Mutagenesis using the Polymerase Chain Reaction" *Gene* 96: 125–128 (1990).

James R. Lupski et al., "Short, Interspersed Repetitive DNA Sequences in Prokaryotic Genomes" *J. of Bacteriology* vol 174, No. 14, pp. 4525–4529 (Jul. 1992).

Hideo Maki et al., "Use of Universal and Type-specific Primers in the Polymerase Chain Reaction for the Detection and Typing of Genital Human Papillomaviruses" *Jpn. J. Cancer Res.* vol. 82 pp. 411–419 (Apr. 1991).

(List continued on next page.)

Primary Examiner—Margaret Parr
Assistant Examiner—Ardin H. Marschel
Attorney, Agent, or Firm—Steven R. Lazar; Thomas J. DesRosier

[57] ABSTRACT

A method for detecting the presence of small mounts of contaminant DNA, present in an amount of at least about 0.1 picogram of DNA, in a protein product produced by recombinant DNA technology. The method comprises using oligonucleotides with sequences directed to those of repetitive host cell line DNA sequences, as primers in a PCR reaction. Also disclosed are kits for the detection of small amounts of contaminant DNA in a protein product.

1 Claim, No Drawings

OTHER PUBLICATIONS

Robert K. Moyzis et al., "The Distributions of Interspersed Repetitive DNA Sequences in the Human Genome" *Genomics* 4: pp. 273–289 (1989).

S. R. Per et al., "Quantitation of Residual Mouse DNA in Monoclonal Antibody Based Products" *Symposium on Monoclonal Antibodies for Therapy, Prevention and in vivo Diagnosis of Human Disease. Utrecht, The Netherlands 1989 Develop Biol. Standard.*, vol. 71 pp. 173–180 (S. Karger, Basel, 1990).

Gary J. Sharples et al., "A Novel Repeated DNA Sequence Located in the Intergenic Regions of Bacterial Chromosomes" Nucleic Acids Research. vol. 18 No. 22 pp. 6503–6508 (1990).

John G. K. Williams et al., "DNA Polymorphisms Amplified by Arbitrary Primers are Useful as Genetic Markers" Nucleic Acids vol. 18 No. 22 pp. 6531–6535 (1990).

Zilla Wong et al., "Cloning a Selected Fragment From a Human DNA 'Fingerprint': Isolation of an Extremely Polymorphic Minisatellite" *Nucleic Acids Research.*, vol. 14 No. 11 pp. 4605–4615 (1986).

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Chinese Hamster
        ( G ) CELL TYPE: Chinese Hamster Ovary ( v i i ) IMMEDIATE SOURCE:
        ( B ) CLONE: CHO alu-equivalent consensus sequence ( v i i i ) POSITION IN GENOME:
        ( C ) UNITS: bp ( x i ) SEQUENCE DESCRIPTION: SEQ ID NO:1:

```
CCAGGCATTG GTGGYACACA CCTTTAGTCC CAGCACTCAG GAGGCAGAGG CAGGAGGATC        60

ACTTGAGTTC HAGAGCCAGC CTGGTCTACC AGAGTTCCTG AGTTCAAGCC AGGCTATACA       120

GAGAAACCCT GTCT                                                         134
```

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Chinese Hamster
        ( G ) CELL TYPE: Chinese Hamster Ovary ( v i i ) IMMEDIATE SOURCE:
        ( B ) CLONE: Primerto CHO alu- equivalent consensus sequence ( v i i i ) POSITION IN GENOME:
        ( C ) UNITS: bp ( x i ) SEQUENCE DESCRIPTION: SEQ ID NO:2:

```
CCAGGCATTG GTGGCAC                                                       17
```

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:

(A) ORGANISM: Chinese Hamster
(F) TISSUE TYPE: Chinese Hamster Ovary (vii) IMMEDIATE SOURCE:
(B) CLONE: Primer Complementary to CHO alu-equivalent consensus seq.

(viii) POSITION IN GENOME:
(C) UNITS: bp (xi) SEQUENCE DESCRIPTION: SEQ ID NO:3:

AGACAGGGTT TCTCTGT    17

DETECTION OF RESIDUAL HOST CELL DNA BY PCR

FIELD OF THE INVENTION

The present invention relates to the detection of nucleic acid contamination in recombinant DNA engineering processes. More specifically, the present invention relates to the use of the polymerase chain reaction (PCR) to detect contaminant DNA in drugs and biologicals produced by recombinant DNA technology.

BACKGROUND

Food and Drug Administration (FDA) regulations recommend that pharmaceutical manufacturers using recombinant DNA processes demonstrate that products contain very low levels of DNA. Current FDA guidelines specify that levels of DNA amounting to less than 10 picograms of DNA per dose should generally be acceptable. *Points to Consider in the Characterization of Cell Lines Used to Produce Biologicals*, Office of Biologics Research and Review, FDA (Nov. 18, 1987).

Current methods for determining the levels of residual DNA in protein product include the Threshold TM Total DNA Assay system (Molecular Devices Corporation, Menlo Park, Calif.), which uses an automated reader to quantitate DNA by detecting the rate of pH change in enzyme-bound DNA samples. This method is disadvantageous in that it is costly, labor intensive, and is restrictive in that specific compatible buffers must be chosen. Further, because of bulk drug substance formulations and assay system volume restrictions which limit sensitivity, a full dose cannot always be tested using this assay.

The polymerase chain reaction (PCR), Mullis et al., Methods in Enzymology, 155:335 (1987) allows nucleic acid sequences up to a few kilobases in length to be amplified in large amounts in a relatively short period of time. Generally, oligonucleotides having DNA sequences directed to a known DNA sequence in a target DNA molecule are used as primers for amplification.

Silver et at., U.S. Pat. 5,104,792, discloses a method by which, using a collection of "universal primers", PCR can be used to amplify viral nucleic acids present in small amounts in clinical material.

Goldman et al., *Clinical Chemistry*, 37:1523 (1991) describe a method by which primers developed to amplify the *E. coli* gene for 16S ribosomal RNA, which is repeated about seven times in the *E. coli* genome, are used as a marker for *E. coli* DNA.

These known processes, however, suffer the disadvantages of requiring DNA primers which are specific to genes present in the host organism genome only in small numbers, and therefore are not capable of being used to detect the presence of DNA contamination on the order of about 1 to 10 picogram. Because of the volume and formulation restrictions, there exists a need for more sensitive methods of detecting DNA contamination present in small amounts, on the order of at least about 0.01 to about 0.1 picogram.

SUMMARY OF THE INVENTION

The present invention allows the detection of contaminant DNA to a high degree of sensitivity by using oligonucleotides directed to repetitive DNA sequences that exist in the genome of the host cell line used in production of recombinant proteins. The present invention is advantageous in that it is low cost, and is able to detect the presence of DNA with increased sensitivity, on the order of at least about 0.1 picogram, and preferably at least about 0.01 picogram of DNA.

Accordingly, it is one object of the present invention to provide a highly sensitive method for the detection of residual DNA in a composition, which method is capable of detecting DNA in amounts of at least about 0.1 picogram, and preferably at least about 0.01 picogram of DNA.

It is another object of the present invention to provide primers which are suitable for use in PCR reactions, in order to detect residual DNA in a composition which is intended to be free of contaminant DNA.

It is one advantage of the present invention that a relatively low cost, and relatively time efficient method for detecting the presence of DNA is a composition is provided.

It is another advantage of the present invention that methods are provided for the detection of the presence of a relatively minor amount of contaminant DNA in a composition. In fact, using the methods of the present invention, DNA present in amounts as small as about 1 femtogram ($1 \times 10^{-15}$ g) of DNA can be detected.

DESCRIPTION OF THE SEQUENCES

SEQUENCE ID No. 1 is the nucleotide sequence for the CHO Alu-equivalent consensus sequence.

SEQUENCE ID Nos. 2 and 3 are the nucleotide sequences of PCR primers to the CHO Alu-equivalent consensus sequence.

DETAILED DESCRIPTION OF THE INVENTION

The above objectives and advantages of the present invention are achieved by a method for detecting contaminant DNA in a protein product using the PCR reaction, said method comprising:

(a) if necessary, digesting the protein product, which may contain a target nucleic acid contaminant to be amplified, and leaving the target nucleic acid contaminant intact;

(b) denaturing the intact nucleic acid contaminant of step (a) to reveal single stranded DNA;

(c) annealing to the single stranded DNA one or more primers, each primer comprising an oligonucleotide directed to repetitive DNA sequences;

(d) extending the primers with a polymerase capable of copying a DNA template;

(e) repeating steps (b) through (d) through multiple rounds sufficient to generate detectable PCR product; and (f) identifying any PCR product obtained from step (e) by standard molecular biological techniques, such as gel electrophoresis, Southern blot, fluorescence spectroscopy, hybridization of immobilized amplified DNA to defined probes, DNA monoclonal antibodies, labelling of the amplified DNA for use as probe in hybridization to immobilized potential target nucleic acids ("reverse" blot), cloning, sequencing, or other molecular biological techniques well know to those of ordinary skill in the art.

Digestion of proteins is usually necessary prior to denaturation of the protein product. If necessary, digestion can be accomplished by means known to those skilled in the art which will leave DNA intact. Preferred means of protein digestion include enzymatic digestion, for example, by Proteinase K. Denaturation of nucleic acids may be accomplished by means known to those skilled in the art for preparing single-stranded DNA. A preferred means of denaturation employs heat.

The primers used in step (c) may consist of a single primer or multiple primers directed to repetitive DNA sequences. Those skilled in the art of PCR will recognize primers which are suitable for amplification of a given repetitive DNA sequence. In the case of minisatellite DNA-directed PCR, the use of a single primer is preferred. In many cases, a pair of primers is used in order to produce a PCR product of definite length. In some cases, it may be preferable to employ a mixture of primers designed to amplify different repetitive DNA sequences present in the genome of a host organism.

In another embodiment, the present invention comprises kits for detecting the presence of small amounts of contaminant DNA in a protein product. The kit of the present invention comprises primers comprising oligonucleotides directed to repetitive DNA sequences; and reagents for performing PCR amplification. In a preferred embodiment of the invention the primers are directed to repetitive DNA sequences which comprise at least about 1% of the genome of a host organism used to produce the protein product. In a further preferred embodiment, the primers used in the kit comprise oligonucleotides directed to the CHO Alu-equivalent consensus sequence.

Unless otherwise defined, all technical and scientific terms used herein shall have the same meaning as commonly understood by one of ordinary skill in the art. Unless mentioned otherwise, the techniques employed or contemplated herein are standard methodologies well known to one of ordinary skill in the art. The embodiments are only illustrative and not limiting. All publications mentioned herein are incorporated by reference.

The oligonucleotides suitable for use as primers within the method or kit of the present invention are sequences which are directed to repetitive DNA sequences in the genome of a host organism, such as *E. coli*, yeast and mammalian cells. These repetitive DNA sequences are thought to appear at least 10 times in the genome, preferably in the organism the genome of which was used to express the protein product. It is preferred that the repetitive DNA sequences comprise at least about 1% of the genome of the host organism. In a preferred embodiment of the present invention, the oligonucleotide primers are directed to repetitive DNA sequences in the genome of Chinese hamster ovary (CHO) cells. The oligonucleotide primers of the present invention may be of any length suitable for use in PC R reactions, preferably at least about 8 base pairs in length. In a preferred embodiment of the present invention, the primers are from about 8 to about 30 bases in length. In a more preferred embodiment, the primers are from about 9 to about 20 bases in length.

The Alu family of interspersed repetitive DNA sequences is present in most or all mammalian genes, including mouse, CHO and human, in an amount of approximately 3 to 6% of the genome. Lupski and Weinstock, J. Bacteriology, 174:4525–4529 (1992). In a preferred embodiment, the first oligonucleotide primer used in the present invention has a sequence complementary to a region of the CHO Alu-equivalent consensus sequence; the second primer has an oligonucleotide sequence identical to a different region of the CHO Alu-equivalent consensus sequence. Haynes et al., *Molecular and Cellular Biology*, 1:573–583 (1981), the text of which is hereby incorporated by reference. In another preferred embodiment, a pair of oligonucleotide primers are used. One of the primers has a sequence which is complementary to the 5' or 3' terminal sequence of the 134 base pair CHO Alu-equivalent consensus sequence. The second primer has a sequence which is identical to that of the 3' or 5' terminal sequence of the CHO Alu-equivalent consensus sequence. The CHO Alu-equivalent consensus sequence is given in Seq. ID No. 1.

Primers directed to minisatellite DNA sequences may be used in the present invention. Minisatellite regions of human DNA are described in Jeffreys et at., *Nature* 313:67–72 (1985); and Wong et at. *Nucleic Acids Research* 14:4605–4615 (1986).

Other repetitive DNA sequences are described in the literature. See, Jelinek and Schmid, *Ann. Rev. Biochem.*, 51:813–844 (1982); Moyziz et at., *Genomics*, 4:273–289 (1989); Lupski and Weinstock, supra; Sharples, *Nucleic Acids Research*, 18:6503–6508 (1990); Eisenach et al., *J. Infectious Diseases*, 161:977–981 (1990).

It is understood that the examples and embodiments described in the examples below are for illustrative purposes only and that various modifications or changes in light thereof will be suggested to persons skilled in the art and are to be included within the spirit and purview of this application and scope of the appended claims.

Modification of materials and conditions, such as use of different DNA polymerases, and altering the temperature at which priming is performed, are easily accomplished by one skilled in the art and are within the present invention.

EXAMPLES

EXAMPLE 1: PCR Materials and Methods

Polymerase chain reactions (PCR) are performed in a volume of 100 μL containing 10 mM Tris-HCl, pH 8.3, 50 mM KCl, 1.5 mM $MgCl_2$, 0.001% (w/v) gelatin, 1 μM each oligonucleotide primer, and 200 μM each dATP, dCTP, dGTP, dTTP (Pharmacia) with 2.5 units *Thermus aquaticus* polymerase (Perkin Elmer-Cetus) and DNA template. Ampliwax PCR Gems (Perkin Elmer-Cetus) are used according to the manufacturer's instructions. Reactions are carried out in a DNA Thermal Cycler (Perkin Elmer-Cetus). Following denaturation of the DNA at 95° C. for 2 minutes, 40 cycles are performed consisting of denaturation at 95° for 1 min., primer annealing at 52° C. for 1 min., and primer extension at 72° C. for 1 minute.

In the experiment above, the following pair of primers to the CHO Alu-equivalent consensus sequence may be used:

(i) 5' CCAGGCATTG GTGGCAC 3'
(ii) 5' AGACAGGGTT TCTCTGT 3'

Primer (i) is identical to the first 17 bases of the 5' end of the CHO Alu-equivalent consensus sequence. Primer (ii) is complementary to the first 17 bases of the 3' end of the CHO Alu-equivalent consensus sequence.

Amplified products are analyzed by electrophoresis on a 2% (w/v) agarose gel containing 0.4μg of ethidium bromide per milliliter and visualized on a ultraviolet transilluminator. Total DNA is quantitated using the fluorochrome Hoescht 32258.

EXAMPLE 2: Booster Method for PCR Reactions

In order to increase the sensitivity of the PCR reaction of Example 1, Booster PCR may be employed. This involves diluting the primers to approximately 10–100 pM (providing a $10^7$-fold molar excess of primer with respect to the expected amount of target) for the first 10 cycles. Cycling for these first 10 cycles consists of denaturation at 95° C. for one min., annealing at 52° C. for 2 min., and extension at 72° C. for 1 minute. At the end of this first round of cycles, primer concentrations are adjusted up to 1 μM each and 45 additional cycles are run according to the following: denaturation at 90° C. for 1 min., annealing at 52° C. for 1 min., and primer extension at 72° C. for 1 minute.

---

What is claimed is:

1. A method for detecting residual DNA from a mammalian host organism in a recombinant protein product, said method comprising:
   (a) preparing a recombinant protein product using a mammalian host through standard molecular biological techniques using a mammalian host cell;
   (b) if necessary, digesting the recombinant protein product of step (a), which may have a target nucleic acid contaminant to be amplified, leaving target nucleic acid contaminant intact;
   (c) denaturing the intact residual DNA of step (b) to reveal single stranded residual DNA;
   (d) annealing to the single stranded residual DNA of step (c) one or more oligonucleotide primers, each oligonucleotide primer comprising an oligonucleotide directed to the DNA sequence of SEQ ID NO:1;
   (e) extending the oligonucleotide primers of step (d) with a polymerase capable of copying a DNA template;
   (f) repeating steps (c) through (e) through multiple rounds sufficient to generate detectable PCR product from the single stranded residual DNA; and
   (g) detecting the presence of residual DNA in the recombinant protein product by identifying any PCR product generated in steps (c) through (f), wherein such identification is accomplished by standard molecular biological techniques.

* * * * *

UNITED STATES PATENT AND TRADEMARK OFFICE
CERTIFICATE OF CORRECTION

PATENT NO. : 5,393,657
DATED : February 28, 1995
INVENTOR(S) : Letwin et al.

It is certified that error appears in the above-identified patent and that said Letters Patent is hereby corrected as shown below:

In line 1 of the Abstract, please change "mounts" to -- amounts --.

Signed and Sealed this

Twenty-ninth Day of August, 1995

Attest:

BRUCE LEHMAN

*Attesting Officer*   *Commissioner of Patents and Trademarks*